United States Patent [19]

Sakamoto et al.

[11] Patent Number: 4,713,247

[45] Date of Patent: Dec. 15, 1987

[54] LONG-ACTING FORMULATION OF CEFACLOR

[75] Inventors: Teruo Sakamoto; Sadao Kawai, both of Osaka; Kinzaburo Noda; Toyohiko Takeda, both of Hyogo; Hiroshi Kato, Miyagi, all of Japan

[73] Assignee: Shionogi & Co., Ltd., Osaka, Japan

[21] Appl. No.: 615,242

[22] Filed: May 30, 1984

[30] Foreign Application Priority Data

Jun. 15, 1983 [JP] Japan ................... 58-108289

[51] Int. Cl.$^4$ ............... A61K 9/62; A61K 9/58; A61K 31/78; A61K 31/675

[52] U.S. Cl. .................... 424/461; 424/462; 424/81; 514/200

[58] Field of Search ............ 424/19, 32, 81, 461, 424/462; 514/208, 209, 200

[56] References Cited

U.S. PATENT DOCUMENTS 4,250,166  2/1981  Maekawa ................... 514/209

OTHER PUBLICATIONS

Chemical Abstracts vol. 101:3821h, The Superior Antibacterial Affect of Cefaclor Over Cephalexin in vitro Against Gram-Negative Aerobis.

*Primary Examiner*—Jerome D. Goldberg
*Attorney, Agent, or Firm*—Wenderoth, Lind & Ponack

[57] ABSTRACT

Highly potent long-acting formulation of cefaclor for treating bacterial infections in human or animals, comprising a rapid-release and a slow-release component at a ratio of about 3:7 to about 5:5 by potency of cefaclor, convenient for administration or carrying about.

5 Claims, 8 Drawing Figures

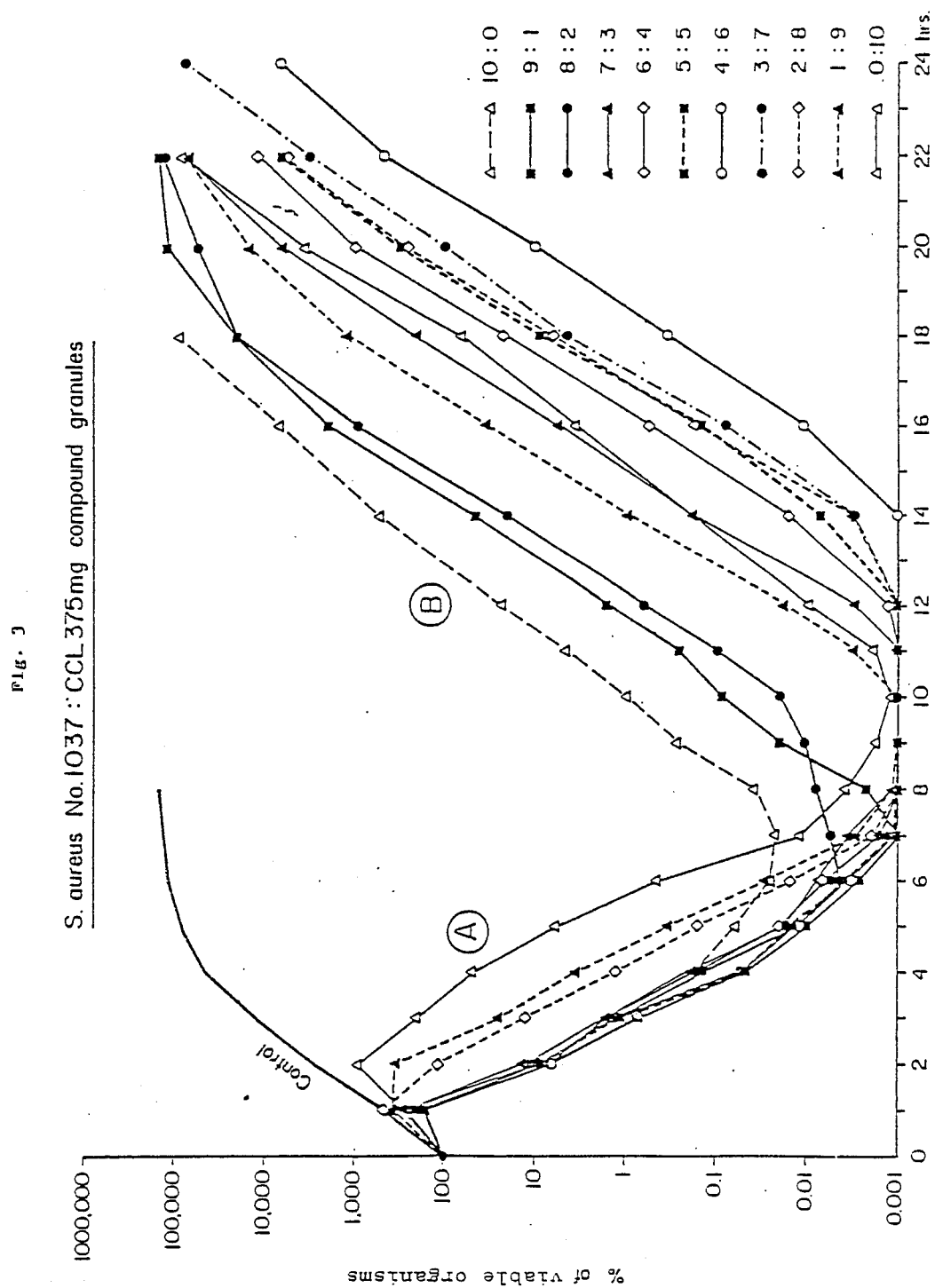

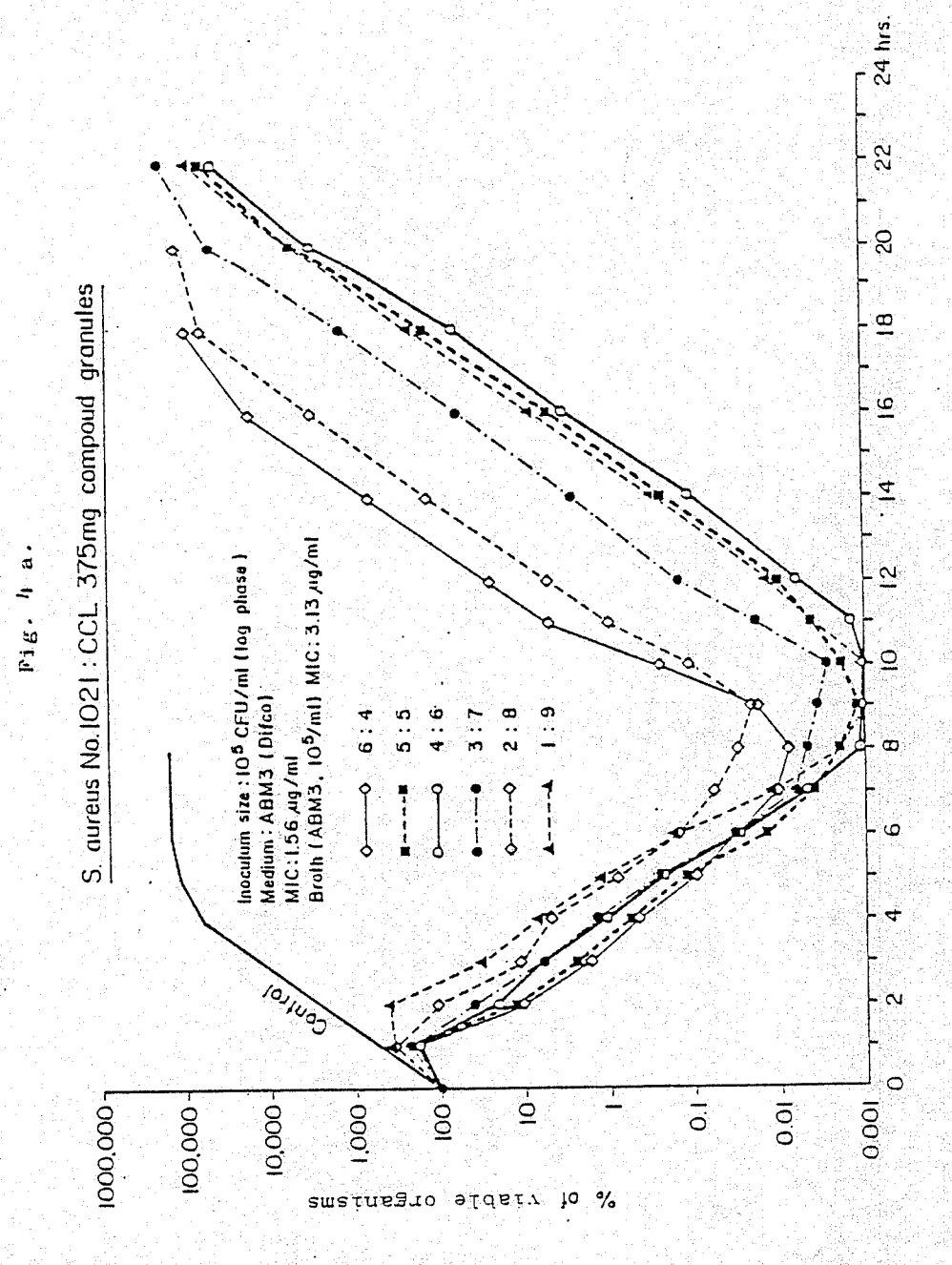

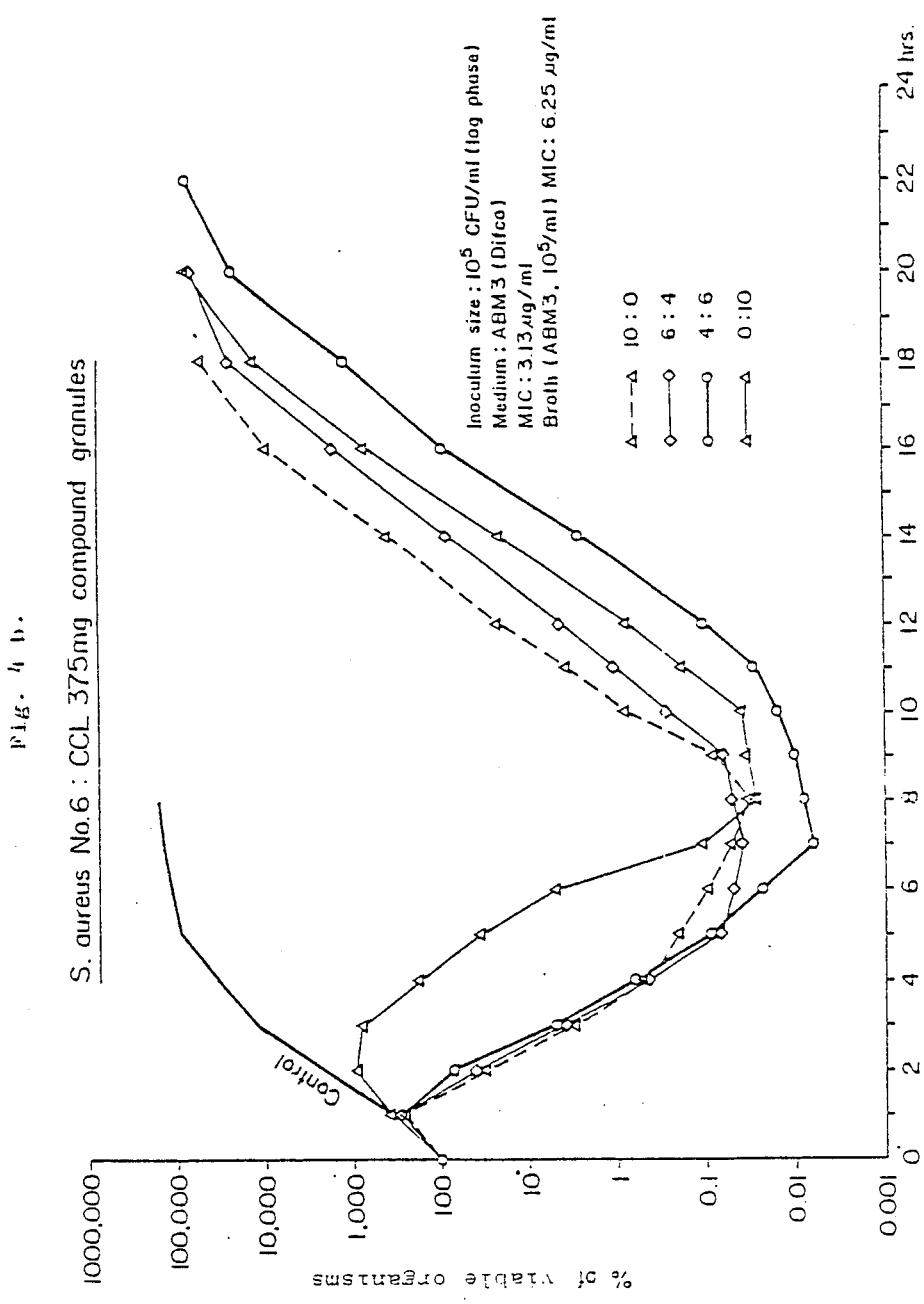

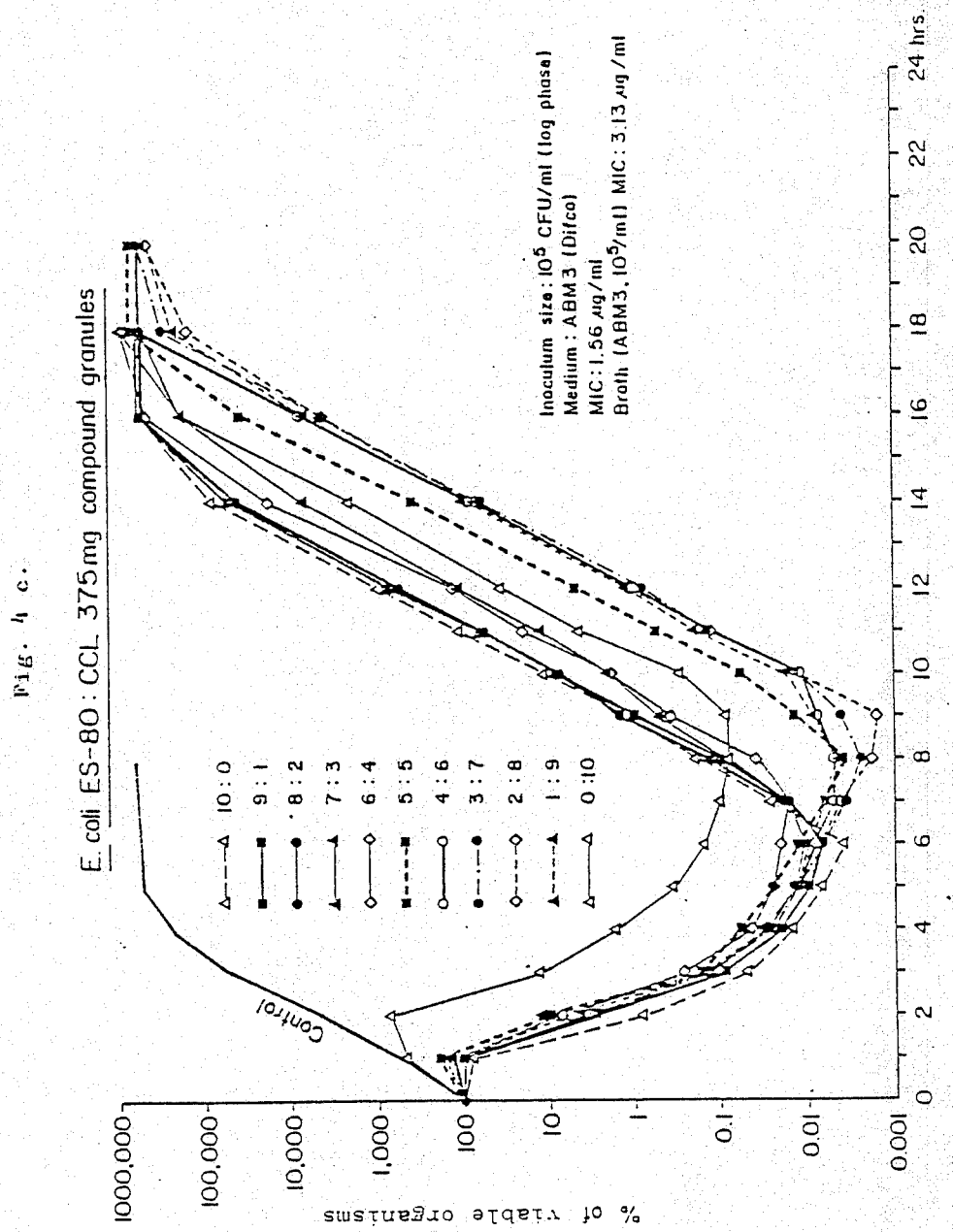

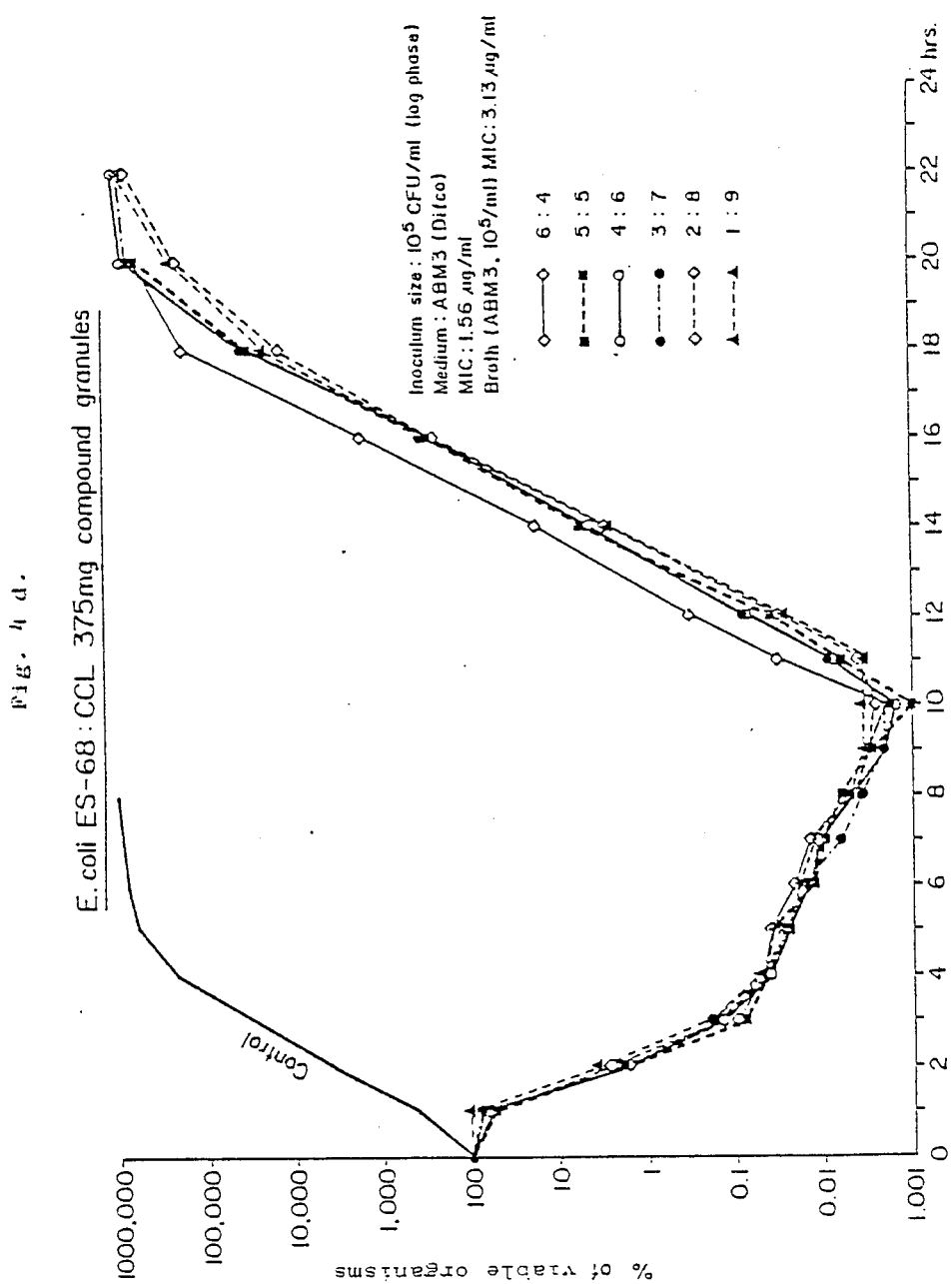

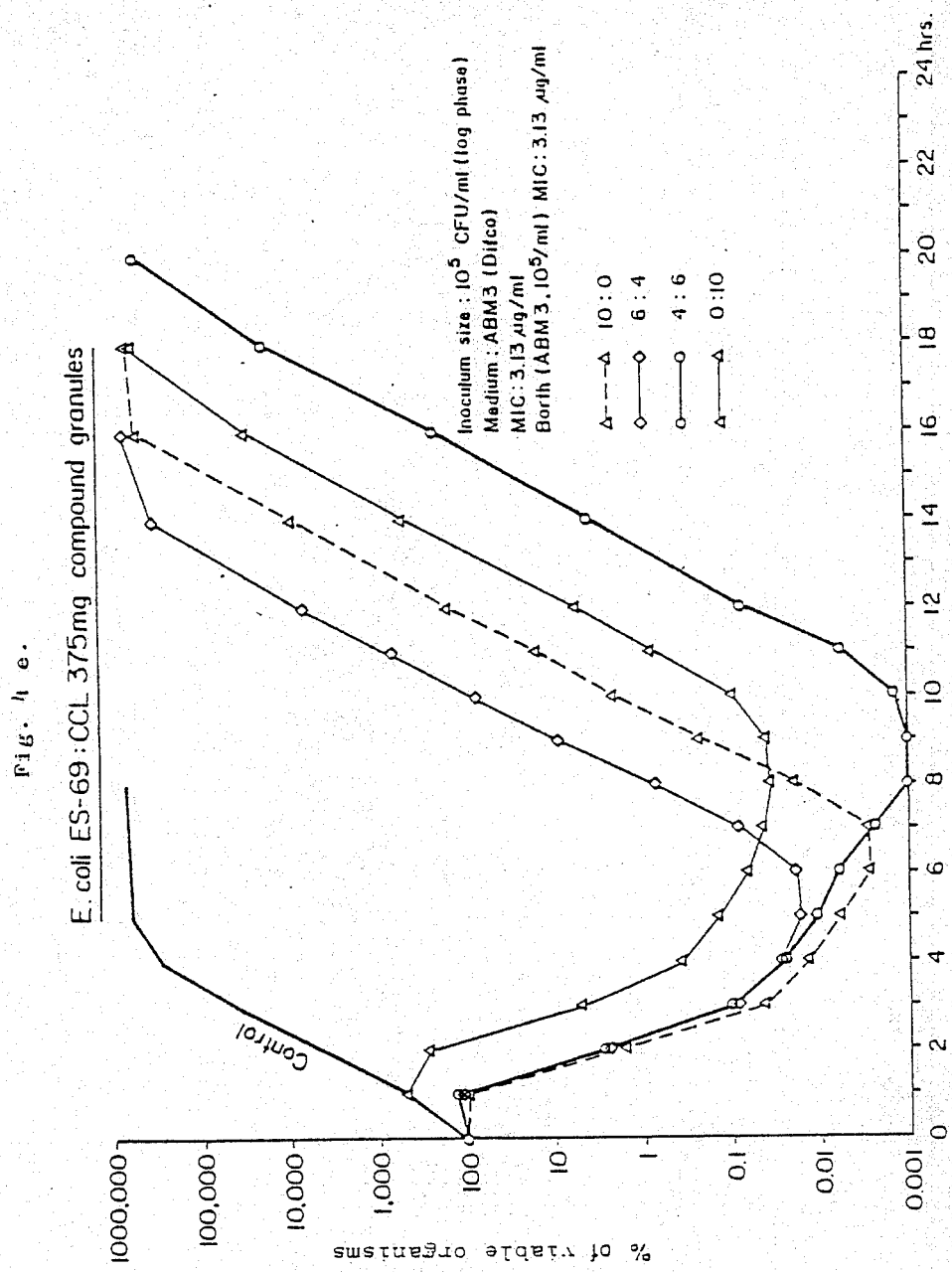

LONG-ACTING FORMULATION OF CEFACLOR

BACKGROUND OF THE INVENTION

1. Field of the Invention

The present invention relates to the field of pharmaceutical preparations and provides new oral long-acting formulations of a cephalosporin-type antibiotic, cefaclor [3-chloro-7-D-(2-phenylglycinamido)-3-cephem-4-carboxylic acid monohydrate] (hereinafter referred to as CCL).

2. Description of the Prior Art

CCL was developed in U.S.A. as an orally administrable cephalosporin antibiotic which has a broader spectrum and is 2 to 8 times more active than an analogue, cefalexin (hereinafter referred to as CEX) in an in vitro antimicrobial test. The antibiotic CCL has ordinarily been applied in treatment of a variety of infections since it has a more potent bactericidal action than CEX and is highly effective in clinical use. The formulation of CCL presently marketed, however, must be administered 3 times a day, i.e., at intervals of eight hours; the time of administration is not necessarily in accordance with the ordinary meal-time, and such disadvantages are naturally desired to be removed. L-Keflex (Lilly's brand of long-acting CEX formulation) is representative of long-acting oral formulation of antibiotics which has been marketed [disclosed in U.S. Pat. No. 4,250,166 (Japanese Patent Publication No. 55-47611)].

SUMMARY OF THE INVENTION

A long-acting formulation of CCL comprises a rapid-release and a slow-release component of CCL at a ratio of about 3:7 to about 5:5 by potency of CCL; the former component is formulated to give a maximum blood level of CCL rapidly and the latter within a period of 3 to 7 hours after the administration.

BRIEF DESCRIPTION OF THE DRAWINGS

The respective chart a. or b.

FIG. 3 shows curves of viable cells versus time relationship in the case that the simulated blood CCL level responding to the respective combination ratio (rapid : slow) of long-acting CCL formulation had influence on the viable cell number of *Staphylococcus aureus* No. 1037 in a culture medium; the axes of ordinate and abscissa show percentage of the viable cell number to the inoculum size of test microorganism and time (hours), respectively.

The respective charts a. to e. in FIG. 4 show curves of viable cell number versus time relationship at respective combination ratio concerning to *Staphylococcus aureus* No. 1021, *Staphylococcus aureus* No. 6, *Escherichia coli* ES-80, *Escherichia coli* ES-68, *Escherichia coli* ES-69, as in FIG. 3; the axes of ordinate and abscissa show percentage of the viable cell number to the inoculum size of the test microorganisms and time (hours), respectively.

DESCRIPTION OF THE PREFERRED EMBODIMENT

The present invention relates to long-acting formulation of CCL (hereinafter referred to as long-acting CCL), more particularly, it relates to long-acting CCL which comprises rapid-release component of CCL and slow-release component of CCL: the former component is formulated so as to release the active ingredient immediately after the administration and the latter is formulated into film-coated formulations covered with an enteric-coating film soluble at pH 5.0 to 7.0, preferably at pH 5.5 to 6.5.

As mentioned above, the ordinary formulation of CCL requires every eight-hours administration to give the best efficacy. It is, however, usually administered after each meal because the administrations precise at 8 hour intervals are practically inconvenient.

In many cases, normal meals three times a day are usually taken rather in the daytime: therefore, there is an intermission of about 12 hours from an evening meal (supper) to a next morning one (breakfast). Furthermore, such every 8 hours administration fixed independent upon each mealtime causes trouble for outpatients because they must keep in mind the exact time for administration without failure.

For patients with slight or moderate infections to whom the ordinary formulation of CCL has mainly been administered, it is desired to provide them with a special formulation of CCL of which the frequency of administration is reduced so that they can take the drug at the prefixed time safely, because they are not always required to be admitted to a hospital, and they have to often take the formulation in school or offices.

The present inventors have attempted to develop the special formulation of CCL by techniques for pharmaceutical preparation, by which the failure of administration is avoided, which may be taken at unified intervals, and which affords the same clinical efficacy at the same daily dose as the ordinary formulation. The present invention is based upon these considerations. In other words, taking into consideration of the fact that breakfast and supper are usually taken at intervals of about 12 hours by most people, it is naturally appropriate to take the drug twice a day after every breakfast and supper.

Thus, it is preferred to regulate the condition of administration, i.e., taking a drug after breakfast and supper, and to take the drug at equal intervals in order to avoid failure of administration and decrease of the clinical efficacy caused by a time lag of administration. In addition, inconvenience imposed on patients who have to always carry the drugs when go out can be avoided.

The present inventors have studied the in vivo distribution of CCL (blood level) and the in vitro antibacterial activity.

Figure 1:
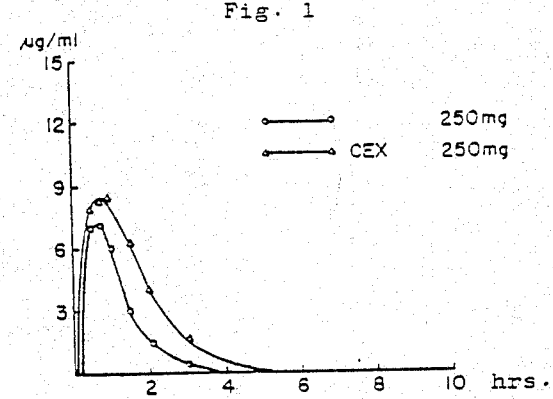
FIG. 1 shows time-dependent curves of mean blood-level when CCL or CEX was administered at a single dose of 250 mg to some volunteers after fasting; the axes of ordinate and abscissa show the concentrations ($\mu$g/ml) of the drugs and the time (hours), respectively.

FIG. 1 shows the blood levels versus time curves when CCL or CEX is administered at a single dose of 250 mg to some volunteers after fasting (details of the tests are described afterwards). The absorption and the excretion of both drugs resemble each other in patterns of the curves, but the maximum blood level is lower and the half-life shorter in CCL than those in CEX.

Figure 2:
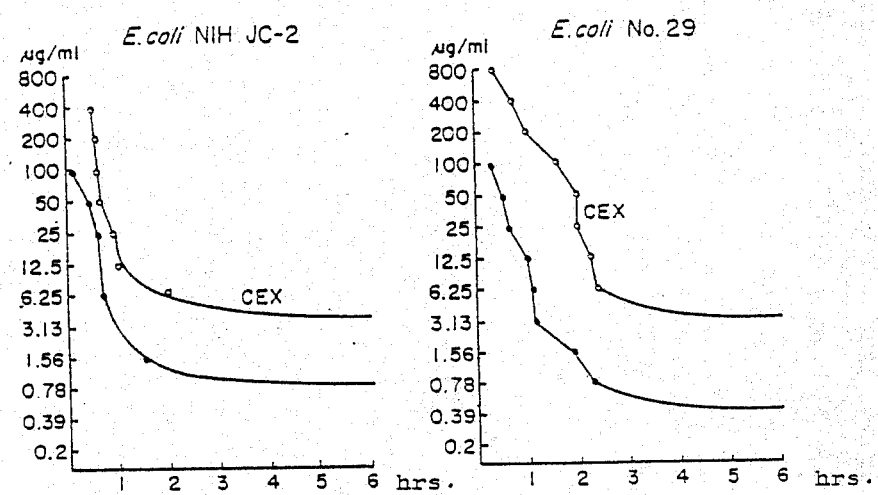
in FIG. 2 shows the differences in both the concentrations of drugs (ordinate) and the period of time (abscissa) which were needed for 99% sterilization of *Escherichia coli* NIH JC2 or *Escherichia coli* No. 29, between CEX and CCL.

Additionally, the bactericidal effects of CCL were compared with those of CEX through the following in vitro tests (details of the tests are described afterwards). The concentrations of CCL or CEX and the time which are needed for diminishing 99% of the inoculum size were measured (FIG. 2, Table 2). As seen from the results of the test, CEX needs at least one MIC (concentration of CEX corresponding to MIC) for diminishing 99% of the inoculum size; on the contrary, sterilizes 99% of the microorganisms even at ½ MIC within a shorter period of time than CEX.

As mentioned above, it was confirmed that the characteristic of CCL was quite different from that of CEX in the concentration and time needed for sterilization as well as in the absorption and excretion.

The present inventors attempted to use a formulation consisting of rapid-release portions and slow-release ones for maintaining the blood level of CCL at over a certain level for a long period of time, and found the optimum combination ratio of the rapid-release component to the slow-release one of CCL (Total amount of CCL in the formulation is 375 mg by potency.) according to the following ways:

1. A rapid-release and a slow-release component are independently prepared.
2. The rapid-release component (375 mg as CCL) is administered to a few volunteers 30 minutes after the meal; the average blood level is determined from the actual values.
3. In the same manner as in the above item 2., the slow-release component (375 mg as CCL) is tested.
4. The blood level in each combination ratio is proportionally calculated from the results in the above items 2. and 3., which is shown by an integral ratio of the rapid-release component to the slow-release one by potency of CCL as 1:9 to 9:1.
5. Time-depending blood level changes in all combinations (rapid:slow=10:0 to 0:10) are simulated in a culture medium, in which the microorganisms are brought into contact with CCL at concentrations changing time-dependently, and then the changes of the viable cell numbers are observed.

The results obtained through the above procedures are illustrated in FIG. 3.

In this test, *Staphylococcus aureus* No. 1037 was chosen as a representative of gram positive bacteria. The respective growth curves in the figure showed a similar tendency concerning:
a. rate of decreasing of the viable cells (i.e., slopes of the curves on the region A), and
b. growth-rate after the bottom (slopes of the curves of the region B), but considerable differences were observed among the respective curves concerning:
i. the time at which the number of the viable cells begin decreasing,
ii. the time at which the cells begin to revive, and
iii. the number of the viable cells at the time of cell revival occuring.

In this connection, it was recognized that the 4:6 formulation (the combination ratio by potency of CCL) satisfied the above items i to iii.

The long-acting formulation of CCL in this invention means those which are composed of rapid-release and slow-release portion, and keep the activity of CCL for a longer period of time than the ordinary formulation of CCL does. The object of this invention is to find out the optimum combination ratio of CCL between the two components.

The long-acting formulation of CCL may be prepared into a multi-layer formulation consisting of rapid-release and slow-release portion, or into a blended formulation which is a mixture of the two independently prepared components at a desired ratio. Additionally, the dosage forms to be prepared may not be limited specifically, and any form may be applied to this invention so far as it is in a conventional form for orally administrable antibiotics. The multi-layer formulation may be formed into granules or beads, which may further encapsulated in capsules or formed into tablets according to the conventional manner. On the other hand, the blended formulation also includes powder, granules, beads, capsules, tablets and the like.

In this invention, the rapid-release portion (or component) means plain formulations of CCL to which no treatment for retardation nor enteric coating-film is given. Therefore, the rapid-release portion may be unprocessed powder of CCL, or granules, beads or tablets prepared in the conventional manner.

The slow-release portion (or component) means microcapsules prepared from unprocessed powder of CCL by film-coating, or enteric coated formulations prepared from granules or beads as mentioned above. The slow-release portion plays an important role in retardation of CCL in this invention: the slow-release portion (or component) may be prepared as explained below in more detail.

Since the main absorptive organ for CCL is the upper part of small intestine as well as in CEX, it is necessary to prepare the slow-release portion so that it completely and rapidly releases CCL within a pH range of about 5.0 to 7.0 in order to increase the absorption rate of CCL. Additionally, since the slow-release portion is formulated into a long-acting formulation in combination with a rapid-release portion, it is necessary for the slow-release portion to be insoluble in acidic media, i.e., in the stomach. In this connection, the aforementioned problems are resolved by coating a desirably soluble component (a bare component) with an enteric coating-film which is soluble at pH 5.0 to 7.0, preferably at pH 5.5 to 6.5. In brief, the slow-release portion is prepared from the bare component by covering with such a film.

The excipients employed in preparing the slow-release portion of this invention may be used at a rate of up to 75% (0 to 75%), preferably 15 to 50% by weight to the total amount of the bare component of the slow-release portion depending on the aimed dosage form. The preparation of the lowest limit, i.e., 0% means, for example, microcapsules and the like: since CCL per se is well absorbed in the upper part of the small intestine, it may be formulated into microcapsules covered with a film soluble at pH 5.0 to 7.0, preferably at pH 5.5 to 6.5 by the known methods for microcapsulation, and additionally in order to increase the absorption rate, it may be formulated once into powder with suitable additives, and then into microcapsules by the aforementioned methods.

The excipients, which are usually employed at the ratio mentioned above, include additives for preparing powder, fine granules, granules, beads and the like, such as sugars, sugar alcohols, starches and celluloses. Sugars such as dextrose, sucrose and lactose; sugar alcohols such as D-mannitol, sorbitol and insitol; starches such as wheat starch, corn starch and potato starch; and cellulose (high molecular compounds) such as crystalline cellulose, carboxymethylcellulose (hereinafter referred to as CMC). carboxymethylcellulose calcium (CMC-Ca), hydroxypropylcellulose (HPC), low-substituted hydroxypropylcellulose (L-HPC) and hydroxypropylmethylcellulose (HPMC) are exemplified. One or more additives selected from them may be added to the formulation at the aforesaid ratio; preferably taking into consideration of the desired dissolution rate and stability of the formulation, it is appropriate to use at least one additive selected from the group consisting of D-mannitol, corn starch, crystalline cellulose and lower-substituted hydroxypropylcellulose as the excipients.

Additionally, suitable binders, if desired, with suitable lubricants, disintegrators, excipients and the like are employed in preparing powder, fine granules, granules and beads in a conventional manner. The kind of binders and their amount to be added must be carefully determined since they greatly influence the dissolution rate of CCL. The binders employed includes methylcellulose (MC), HPC, L-HPC, HPMC, dextrin, gelatin, starch and the like.

It is generally difficult to fix the amount and kind of binders to be added because they vary with the dosage form, the density of the formulation, and the amount and kind of the excipients used; it is preferable to prepare the bare component (uncoated slow-release portion) so as to rapidly release the active ingredient. For example, when D-mannitol and MC are respectively employed as excipient and binder in preparing bare granules by a wet granulation method, they are usually added at rates of 18 to 23 wt % and 0.9 to 1.3 wt %, respectively.

The bare component prepared in such a manner is covered with an enteric coating film soluble at pH 5.0 to 7.0, preferably pH 5.5 to 6.5 to give the slow-release component. Detailed explanation for the enteric coating film is as follows.

Generally in this invention, enteric coating substances usually employed in preparing an enteric formulation are applied onto the bare component in a conventional manner; more particularly, it is appropriate to prepare the enteric coating film as to strongly resist acid but rapidly dissolve at pH 5.0 to 7.0, preferably pH 5.5 to 6.5 in order to prolong the action of CCL in the formulation in this invention, since the absorption site for CCL is located in a limited part.

The enteric coating substances employed include phthalic acid celluloseacetate, hydroxypropylymethylcellulosephthalate (HPMCP), polyvinyl alcohol phthalate, carboxymethylethylcellulose, a copolymer of styrene and maleic acid, and a copolymer of methacrylic acid and methyl methacrylate, and if desired, they may be employed with suitable plasticizers and/or extending agents.

The thus prepared slow-release components are combined with the rapid-release ones in the aforementioned ratio to give long-acting formulations of CCL in this invention. Rapid-release component in this invention means a rapid-release formulation per se or a portion of the longacting formulation, which is well disintegrated and dissolved in the stomach. The component may be used in any dosage form; for example, powder, fine granules, granules or tablets which are prepared by admixing CCL with suitable excipients, if desired, along with lubricants and the like; or native CCL (not formulated) can also be applied. Additionally, the aforementioned bare component, which means an uncoated portion of the slow-release component, can also be applied as the rapid-release one. More particularly, the rapid-release component may be a portion of multi-layer granules or beads which is prepared by spray-coating the rapid-release component onto the slow-release component prepared above. In preparing the multi-layer formulations, the thickness of the layer to be coated as a rapid-release portion needs to be estimated so that the ratio of the rapid-release portion to the slow-release one (by potency of CCL) is desired one.

(Effects)

Thus prepared long-acting formulation of CCL in this invention was tested on some microorganisms or strains (FIG. 4; Experiment 4) other than those mentioned before in the same manner as in FIG. 3 (Experiment 3). As a consequence, it was confirmed that the 4:6 formulation (by potency of CCL) which was expected to be the best mode gave satisfactory results for all the aforementioned items i. to iii. on all strains of the microorganisms. In other words, at the blood-levels obtained by the 4:6 formulation of CCL, the test microorganisms are sterilized rapidly and strongly and the effect is maintained over a long period of time.

These facts suggest that the formulation of this invention gives sufficient clinical efficacy at less frequent administration, i.e., twice a day, than the ordinary formulation does at the same daily dose without increase of the daily dose. In fact, it was recognized that the clinical efficacy of the formulation of this invention was comparable to or better than that of the ordinary formulation which was applied three times a day.

The long-acting formulations of CCL in this invention increase the antimicrobial activity through the long-acting effect, and are beneficial in being handy and simple in administration as mentioned above. Therefore, it is advantageous that decrease of the clinical efficacy by failure of administration, which has often occurred in the ordinary formulation, can be avoided by the formulation of the present invention.

As mentioned above, the long-acting formulations of CCL of the present invention act continuously and directly on microorganisms to greatly increase the clinical efficacy of CCL along with prevention of the failure of administration.

EXPERIMENT 1

Comparison between CEX and CCL on the blood levels(FIG. 1)

(1)Drugs:

250 mg Capsules of Keflex® (Shionogi & Co., (LTD-Lilly) as CEX and 250 mg capsules of Kefral® (Shionogi & Co., LTD-Lilly) as CCL were employed.

(2)Subjects (12 volunteers; cross-over testing):

The subjects, 12 healthy and adult men aged 21 to 39 years with 1.58 to 1.83 $m^2$ in the body surface area.

(3)Administration:

To each subject after fasting, who had no meal after supper of the previous day, were given orally the capsules with 100 ml of warm water, and the fasting was continued for 2 hours, except giving them a prefixed amount of water. CEX and CCL were given to the 12 subjects in a cross-over method, and any drugs other than CEX or CCL were not applied for one week.

(4)Measurement:

The blood was collected 8 times, just before the administration, after 0.5, 0.75, 1, 1.5, 2, 3 and 6 hours. The plasma was centrifugally separated under cooling immediately after each collection, rapidly frozen and then preserved at $-20°$ C. until the time of measurement.

The measurement were made within a week after the collection. After the frozen samples were allowed to melt at 4° C., a series of ten-fold dilution was prepared with 0.1M of phosphate buffer (pH 6.0), on which the blood level was measured by a band culture method using *Micrococcus luteus* ATCC 9341 as standard. Antibiotic Medium No. 8 (Difco; hereinafter referred to as ABM 8) was employed as a medium.

(5) Result:

CEX and CCL resembled each other in the trends of the blood level curves, but it was confirmed that CCL showed lower maximum blood level and excreted faster than CEX.

EXPERIMENT 2

Time and concentration required for 99% sterilization (FIG. 2)

(1) Test organisms and the susceptibilities

TABLE 1

| Test Microorganism | MICs ($\mu$g/ml) | |
|---|---|---|
| | CCL | CEX |
| *Escherichia coli* NIH JC-2 | 3.13 | 6.25 |
| *Escherichia coli* No. 29 | 1.56 | 3.13 |

Note:
Minimum Inhibitory Concentrations (MICs) were assayed according to the dilution method disclosed in Chemotherapy 29(1), 76–79 (1981).

(2) Medium:

Heart infusion broth (Nissui Pharmaceutical Co.)

(3) Test method:

The test microorganisms at the logarithmic growth phase (about $10^6$ CFU/ml) were spread into the aforementioned broth placed in tubes, to which CCL or CEX was applied at prefixed serial concentrations. Changing in the number of viable microorganisms was monitored in order to measure the time required for 99% sterilization of the inoculum size in each tube.

(4) Result:

In order to diminish 99% of the inoculum size, CEX needed to be applied at a concentration of one or more MICs, but CCL was effective at a lower concentration, i.e., even at ½ MIC. It was also recognized that the time required for 99% sterilization by CCL was much shorter at any MIC of ½ to about 64 than for CEX.

TABLE 2

| | Time for 99%-sterilization | | | | |
|---|---|---|---|---|---|
| | 4 MIC | 2 MIC | 1 MIC | ½ MIC | ¼ MIC |
| a. *E. coli* NIH JC-2 | | | | | |
| CCL | 0° 35' | 0° 35' | 1° 00' | 1° 30' | — |
| CEX | 0° 55' | 1° 00' | 2° 00' | — | — |
| b. *E. coli* No. 29 | | | | | |
| CCL | 1° 00' | 1° 05' | 2° 00' | 2° 10' | — |
| CEX | 2° 10' | 2° 20' | — | — | — |

EXPERIMENT 3

Growth-curve on the stimulation of single-dose blood-level (FIG. 3);

(1) Test microorganism:

*Staphylococcus aureus* No. 1037

(2) Susceptibility of the test miocroorganisms (MIC value):

1.56 $\mu$g/ml: The value was determined by the above-identified method, where Muller-Hinton agar (Difco) as the medium was employed. Method 1.

3.13 $\mu$g/ml: The value was determined by use of another medium, i.e., Antibiotic medium No. 3 (Difco; hereinafter referred to as ABM 3) broth in which the MIC was measured 18 to 20 hours after the inoculation ($10^5$ CFU/ml. Method 2.

(3) Test method:

Time-dependent changes of the CCL blood levels were simulated in ABM 3 broth by means of computer simulation based on the CCL blood-level-curves which were obtained in Experiment 5. The number of the viable cells after the inoculation ($10^5$ CFU/ml) was monitored from time to time in the broth containing CCL at concentrations simulated by computer.

Such experiments were carried out on the CCL blood levels (at a dose of CCL 375 mg by potency) which were obtained from 11 kinds of 0:10 to 10:0 formulations (rapid: slow by potency of CCL). Results are illustrated in FIG. 3.

(4) Result:

In the growth-curves on 11 kinds of the formulations, the rate of decreasing the viable cells (slopes of the curves on the region A.) and the increasing-rate after the revegetation of them (slopes of the curves on the region B.) were very close; but there was significant differences in each datum on 11 formulations, i.e., the time when the viable cells began to decrease, the time and the number of viable cells when they began to increase. Above all, the formulations of 10:0 to 3:7 (rapid:slow) began to decrease the viable cells earlier than the others; in the formulations of 6:4 to 1:9 (same meaning as defined above) the revival of the organism was much delayed and the number of viable cells at that time was lesser.

Particularly, it was found that the 4:6 formulation satisfied all the conditions, and the starting of revival was most delayed, at which time the number of viable cells was the least.

EXPERIMENT 4

Growth-curve on simulation of a single dose (FIG. 4)

The same procedures as in Experiment 3. were applied to the following strains. The following MIC values were also determined according to the same method as in Experiment 3.

TABLE 3

| | Test Microorganism | MICs ($\mu$g/ml) | |
|---|---|---|---|
| | | $10^6$CFU/ml[*1] | $10^5$CFU/ml[*2] |
| Gram (+) | *Staphylococcus aureus* No. 1021 | 1.56 | 3.13 |
| | *Staphylococcus aureus* No. 6 | 3.13 | 6.25 |
| Gram (−) | *Escherichia coli* ES-80 | 1.56 | 3.13 |
| | *Escherichia coli* ES-68 | 1.56 | 3.13 |
| | *Escherichia coli* ES-69 | 3.13 | 3.13 |

Note:
The values with *[1] or *[2] were determined by the method 1 or 2 disclosed in Experiment 3, respectively.

(Result)

In any strains of the microorganisms, the results had a tendency similar to those in Experiment 3. On the basis of the fact, it was confirmed that the 4:6 formulation was preferred in every condition.

EXPERIMENT 5

Blood level of CCL on the rapid-release or slow-release formulation (1) Dosage form, Dose:

491 mg of the rapid-release granules (375 mg as CCL) prepared in Example 2. or 713 mg of the slow-release granules (375 mg as CCL) were administered to the following 4 subjects.

(2) Subjects (4 adult men) applied are:

4 healthy adult men, aged 26 to 46 years, with 53 to 65 kg body-weight.

(3) Manner of administration:

The rapid-release granules identified above were administered to the 4 subjects 30 minutes after regular meals, and the slow-release granules to the same four subjects after one week duration in which no drug was given.

(4) Measurement of CCL in plasma:

Blood samples were collected from the 4 treated subjects at the prefixed times (total 7 times on each subject) as shown in Table 4, and CCL concentrations in the plasma were measured by High Performance Liquid Chromatography (HPLC).

(5) Result:

TABLE 4

| | CCL concentrations in plasma (μg/ml) | | | | | | | | | | | | |
|---|---|---|---|---|---|---|---|---|---|---|---|---|---|
| | (Rapid-release granules) Time (hr) | | | | | | | (Slow-release granules) Time (hr) | | | | | |
| Subject | 0.5 | 1.0 | 2.0 | 3.0 | 4.0 | 6.0 | 8.0 | 1.0 | 2.0 | 3.0 | 4.0 | 6.0 | 8.0 | 10.0 |
| A | 6.51 | 4.48 | 2.36 | 1.38 | 1.04 | 0 | 0 | 0 | 1.82 | 2.53 | 1.38 | 1.92 | 0.34 | 0 |
| B | 3.30 | 3.50 | 3.83 | 4.50 | 2.04 | 0.30 | 0 | 0.23 | 0.55 | 2.08 | 3.11 | 2.15 | 0.33 | 0 |
| C | 5.70 | 4.56 | 3.85 | 2.31 | 0.95 | 0.20 | 0 | 0 | 1.59 | 3.01 | 2.70 | 1.73 | 0.38 | 0 |
| D | 2.07 | 4.37 | 3.88 | 3.53 | 3.18 | 0.40 | 0 | 0 | 0 | 0.22 | 1.56 | 4.39 | 1.01 | 0 |
| Average | 4.40 ± 1.03 | 4.23 ± 0.25 | 3.48 ± 0.25 | 2.93 ± 0.68 | 1.80 ± 0.52 | 0.23 ± 0.09 | 0 | 0.06 ± 0.06 | 0.99 ± 0.43 | 1.96 ± 0.61 | 2.19 ± 0.42 | 2.55 ± 0.62 | 0.52 ± 0.33 | 0 |

TABLE 5

| | | morning | noon | evening | a daily dose |
|---|---|---|---|---|---|
| Group L | granules | CCL (375 mg) | placebo | CCL (375 mg) | CCL 750 mg by potency |
| | capsule | placebo | placebo | placebo | |
| Group R | granules | placebo | placebo | placebo | |
| | capsule | CCL (250 mg) | CCL (250 mg) | CCL (250 mg) | CCL 750 mg by potency |

Table 5. indicates that in Group L, CCL was administered twice a day, i.e., in the morning and the evening, in a form of the long-acting formulation (a daily dose: 750 mg of CCL by potency), and in Group R, 3 times a day, i.e., in the morning, at noon and in the evening, in a form of the ordinary formulation (a daily dose: 750 mg of CCL by potency).

In addition, all sets of the formulations in both groups are prepared in the same form in external appearance so that it is impossible to distinguish one from the other.

(4) Result:

Efficacy was evaluated according to "The criteria for evaluation of antimicrobial agents in oral surgery" edited by Japanese Society of Oral Therapeutics and Pharmacology.

The clinical efficacy in Group L was as high as in Group R.

TABLE 6

| | Clinical Efficacy on the 5th day | | | |
|---|---|---|---|---|
| | Excellent | Well | None | Total |
| Group L | 69 95.5% | 16 | 4 | 89 |
| Group R | 69 96.7% | 18 | 3 | 90 |
| Total | 137 96.1% | 35 | 7 | 179 |

EXPERIMENT 6

Comparison of clinical efficacy by double-blind test between the long-acting formulations and the ordinary one of CCL (1) Subject to be treated:

Patients, aged 15 years or more, with dental infections, which would be expected to respond clinically by treatment with the ordinary formulation at a 750 mg daily dose of CCL (3 divided doses) were selected except the following patients:

a. patient suffering from a functional disorder in the kidney or liver, or other serious disease,
b. patient treated with an antibacterial or antifungal agent or a steriod hormone recently before this test,
c. patient having a history of allergy to cephalosporin- or penicillin-type agents, and
d. patient in pregnancy or in nursing her baby.

(2) Formulation:

The long-acting formulation of CCL was prepared as granules, enclosed with a package, which contain total 375 mg of CCL at a ratio of 4:6 (rapid:slow) by potency. The ordinary formulation was prepared as capsules, each of which contains 250 mg of CCL by potency in an unprocessed formulation. Furthermore, two kinds of placebos completely equal in external appearance to the packages of granules and the capsules were prepared.

(3) Administration:

According to the schedule as shown in the following table, both a package of granules and a capsule were orally administered 3 times a day after meal. In this schedule, each daily dose of CCL is 750 mg by potency in both the long-acting formulation group (Group L) and the ordinary formulation one (Group R).

The administration was continued for 5 days as a rule.

EXAMPLE 1

| Composition | (% w/w) |
|---|---|
| cefaclor | 76.3 |
| lactose | 11.9 |
| corn starch | 7.8 |
| potato starch | 1.5 |
| Moisture | 2.5 |
| Total | 100 |

To a mixture of 1912 g of cefaclor, 298 of lactose and 222 g of corn starch was added 730 g of 5% paste of potato starch. The mixture was kneaded and formulated into granules with a rotary wet granulator, which were then dried at 50° C. for one hour. The dried granules were rounded off by a speed-mill and sifted out to give bare granules A which pass through a 14 mesh sieve but not through a 24 mesh one.

In this invention, the content of cefaclor in the composition is shown by weight rate by potency to the total of the dried granules. This rule is applied in the process for preparing the formulations, too.

EXAMPLE 2

| Composition | (% w/w) |
|---|---|
| cefaclor | 76.3 |
| corn starch | 12.6 |
| L-HPC | 6.4 |
| HPC | 2.1 |
| Moisture | 2.6 |
| Total | 100 |

To a mixture of 1912 g of cefaclor, 356 g of corn starch and 162 g of L-HPC was added 960 g of 5.5% HPC aqueous solution. The mixture was kneaded and then formulated into bare granules B in the same manner as in Example 1.

EXAMPLE 3

| Composition | (% w/w) |
|---|---|
| cefaclor | 76.3 |
| D-mannitol | 6.8 |
| corn starch | 6.7 |
| L-HPC | 6.4 |
| methylcellulose 25 cps. | 1.3 |
| Moisture | 2.5 |
| Total | 100 |

To a mixture of 1912 g of cefaclor, 170 g of D-mannitol, 191 g of corn starch and 162 g of L-HPC was added 940 g of 3.3% aqueous methylcellulose (25 cps). The mixture was kneaded and formulated into bare granules C in the same manner as in Example 1.

The respective bare granules A to C prepared in Examples 1 to 3 contain 763 mg of CCL by potency per gram.

EXAMPLE 4

| Composition | (% w/w) |
|---|---|
| cefaclor | 46.6 |
| lactose | 29.5 |
| corn starch | 19.9 |
| potato starch | 1.6 |
| Moisture | 2.4 |
| Total | 100 |

To a mixture of 1275 g of cefaclor, 808 g of lactose and 618 g of corn starch was added 810 g of 5% potato starch paste, the mixture kneaded and formulated into bare granules D in the same manner as in Example 1.

EXAMPLE 5

| Composition | (% w/w) |
|---|---|
| cefaclor | 46.6 |
| corn starch | 45.3 |
| L-HPC | 3.9 |
| HPC | 1.9 |
| Moisture | 2.3 |
| Total | 100 |

To a mixture of 1125 g of cefaclor, 1243 g of corn starch and 94 g of L-HPC was added 560 g of 8% aqueous HPC. The mixture was kneaded and formulated into bare granules E in the same manner as in Example 1.

EXAMPLE 6

| Composition | (% w/w) |
|---|---|
| cefaclor | 46.6 |
| D-mannitol | 23.6 |
| corn starch | 22.5 |
| L-HPC | 3.9 |
| methylcellulose 25 cps. | 1.1 |
| Moisture | 2.3 |
| Total | 100 |

To a mixture of 1125 g of cefaclor, 570 g of D-mannitol, 616 g of corn starch and 94 g of L-HPC was added 560 g of 5% aqueous methylcellulose (25 cps). The mixture was kneaded and formulated into bare granules F in the same manner as in Example 1. The bare granules D to F prepared in Examples 4 to 6 contain 466 mg of CCL by potency per gram.

EXAMPLE 7

| Composition | (% w/w) |
|---|---|
| cefaclor | 63.4 |
| sucrose | 34.4 |
| Macrogol 6000 | 0.7 |
| HPC | 0.7 |
| Moisture | 0.8 |
| Total | 100 |

An aqueous solution (a mixture of 1220 g of 2% aqueous Macrogol and 1220 g of 2% aqueous HPC) was sprayed onto a mixture of 2250 g of cefaclor and 1220 g of sucrose and dried in a fluidized-bed granulator; the spraying and the drying were repeated to give spherical beads. The beads were sifted out to 32–60 mesh particles as bare beads G. The beads G contain 634 mg of CCL by potency per gram.

EXAMPLE 8

| Composition | (% w/w) |
|---|---|
| cefaclor | 90.0 |
| crystalline cellulose | 6.0 |
| methylcellulose | 2.0 |
| Moisture | 2.0 |
| Total | 100 |

To a mixture of 900 g of cefaclor and 60 g of crystalline cellulose, which was being rotated in a rapid mixer, was sprayed 400 g of 2% aqueous methylcellulose (25 cps) to give spherical beads. The beads were dried at 50° C. for 60 minutes with a flow-type dryer and then sifted out to 30–100 mesh particles as bare beads H.

The beads H contain 900 mg of CCL by potency per gram.

EXAMPLE 9

| Composition | (% w/w) |
|---|---|
| HPMCP | 5.812 |
| white shellac | 0.646 |
| glycerin fatty acid ester | 2.153 |
| talc | 5.389 |
| ethanol | 52.3 |

-continued

| Composition | (% w/w) |
|---|---|
| dichloromethane | 33.7 |
| Total | 100 |

Coating-solution of the above identified composition was prepared. To 1000 g of bare granules A prepared in Example 1 placed in a coating pan of 40 cm in diameter was sprayed 3570 g of the solution in a conventional manner to give slow-release granules A-1. The bare granules, B, C, D, E and F of Examples 2 to 6 were treated in the same manner as shown above to give slow-release granules B-1, C-1, D-1, E-1 and F-1, respectively. The slow-release granules A-1 to C-1 contain 526 mg, and D-1 to F-1 321 mg of CCL by potency per gram, respectively.

EXAMPLE 10

| Composition | (% w/w) |
|---|---|
| Eudragit ® L100 | 5.812 |
| white shellac | 0.646 |
| glycerin fatty acid ester | 2.153 |
| talc | 5.389 |
| ethanol | 86.0 |
| Total | 100 |

The above-identified coating-solution was prepared. In the same manner as shown in Example 9, 3570 g of the above-identified coating solution was sprayed to the bare granules A, B, C, D, E and F prepared in Examples 1 to 6 to give slow-release granules A-2, B-2, C-2, D-2, E-2 and F-2, respectively.

The slow-release granules A-2 to C-2 contain 526 mg and D-2 to F-2 321 mg of cefaclor by potency per gram, respectively.

EXAMPLE 11

| Composition | (% w/w) |
|---|---|
| Eudragit ® S100 | 5.812 |
| white shellac | 0.646 |
| glycerin fatty acid ester | 2.153 |
| talc | 5.389 |
| ethanol | 86.0 |
| Total | 100 |

The above-identified coating-solution was prepared. In the same manner as shown in Example 9, 3570 g of the solution was sprayed to the bare granules A, B, C, D, E and F prepared in Examples 1 to 6 to give slow-release granules A-3, B-3, C-3, D-3, E-3 and F-3, respectively.

The slow-release granules A-3 to C-3 contain 526 mg and D-3 to F-3 321 mg of cefaclor by potency per gram, respectively.

EXAMPLE 12

| Composition | (% w/w) |
|---|---|
| Eudragit ® L30D | 47.2 |
| Macrogol 6000 | 1.4 |
| talc | 4.2 |
| purified water | 47.2 |
| Total | 100 |

The above-identified coating-solution was prepared. Each 1000 g of bare granules A, B, C, D, E and F prepared in Examples 1 to 6 was spray-coated with 2400 g of the solution by a fluidized-bed coating machine to give slow-release granules A-4, B-4, C-4, D-4, E-4 and F-4, respectively.

The slow-release granules A-4 to C-4 contain 526 mg and D-4 to F-4 321 mg of cefaclor by potency per gram, respectively.

EXAMPLE 13

| Composition | (% w/w) |
|---|---|
| cefaclor | 10.0 |
| HPC | 6.7 |
| lactose | 3.3 |
| purified water | 80.0 |
| Total | 100 |

Onto 1000 g of the slow-release granules A-2 prepared in Example 10 was sprayed 3690 g of the suspension prepared according to the above prescription as rapid-release layers conventionally by a fluidized-bed coating machine to give multi-layer granules I.

The ratio of CCL in the rapid-release portion of the multi-layer granules I to that in the slow-release one is 4:6 by potency, where the granules I contain 516 mg of CCL by potency per gram.

EXAMPLE 14

In a conventional manner using a fluidized-bed coating machine, 3970 g of the coating-solution prepared in Example 10 was sprayed to 1000 g of the bare beads G prepared in Example 7 to give slow-release beads J. The beads J contain 423 mg of CCL by potency per gram.

EXAMPLE 15

In a conventional manner using a fluidized-bed coating machine, 3970 g of the coating-solution prepared in Example 10 was sprayed to 1000 g of the bare beads H prepared in Example 8 to give slow-release beads K. The beads K contain 600 mg of CCL by potency per gram.

EXAMPLE 16

Both the rapid-release granules and the slow-release ones as shown in the following items were packed into strip-packages (hereinafter referred to as SP) to give blended formulations. The ratio of CCL in the rapid-release portion to that in the slow-release one is 4:6 by potency, where they contain 375 mg of CCL by potency per package. The following items show the amounts of the corresponding granules to be packed in one package.

(1) 196 mg of granules B and 428 mg of granules A-1
(2) 322 mg of granules D and 428 mg of granules B-3
(3) 322 mg of granules F and 428 mg of granules C-2
(4) 196 mf of granules C and 700 mg of granules D-4
(5) 322 mg of granules E and 700 mg of granules F-2

Thus, five kinds of blended granules (SP) were prepared.

EXAMPLE 17

Both the following rapid-release and slow-release formulations were filled into a hard-type capsule to give six different kinds of capsules of long-acting CCL.

The ratio of CCL in the rapid-release portions to that in the slow-release ones is 3.5:6:5 by potency, where they contain 187.5 mg of CCL by potency per capsule.

The contents below are shown by the weight of granules or beads to be filled into a capsule.

(1) 86 mg of the granules A and 232 mg of the granules A-3
(2) 86 mg of the granules C and 232 mg of the granules B-1
(3) 141 mg of the granules E and 232 mg of the granules C-2
(4) 141 mg of the granules D and 232 mg of the granules C-4
(5) 103 mg of the beads G and 288 mg of the beads J
(6) 73 mg of the beads H and 203 mg of the beads K

EXAMPLE 18

According to the procedures shown in Example 17, the capsule-formulations of long-acting CCL, which contain 187.5 mg of CCL by potency per capsule, were prepared. The ratio of CCL in the rapid-release portions to that in the slow-release ones is 4:6 by potency.

(1) 161 mg of the granules F and 214 mg of the granules B-3
(2) 98 mg of the granules A and 350 mg of the granules D-1
(3) 98 mg of the granules B and 214 mg of the granules A-4
(4) 98 mg of the granules C and 214 mg of the granules C-2
(5) 83 mg of the beads H and 266 mg of the beads J Thus, five different kinds of capsules were prepared.

EXAMPLE 19

According to the procedures shown in Example 17, the capsules of long-acting CCL formulation, which contain 187.5 mg of CCL by potency per capsule, were prepared. The ratio of CCL in the rapid-release portions to that in the slow-release ones is 4.5:5:5 by potency.

(1) 111 mg of the granules B and 321 mg of the granules E-1
(2) 111 mg of the granules C and 321 mg of the granules F-2
(3) 181 mg of the granules E and 196 mg of the granules A-3
(4) 181 mg of the granules D and 196 mg of the granules C-4
(5) 133 mg of the beads G and 172 mg of the beads K Thus, five different kinds of capsules were prepared.

What is claimed:

1. A long-acting formulation of cefaclor which comprises a mixture of a non-enteric coated component of cefaclor as a rapid-release component with an enteric coated component of cefaclor as a slow release component at a ratio of about 4:6 based on the potency of cefaclor respectively, wherein:

said rapid release component contains at least one additive selected from the group consisting of lactose, sucrose, D-mannitol, corn starch, wheat starch, and low-substituted hydroxypropylcellulose in an amount of up to 75 wt % based on the whole rapid-release component; and said slow-release component contains at least one additive selected from the group consisting of lactose, sucrose, D-mannitol, corn starch, wheat starch, and low-substituted hydroxypropylcellulose in an amount of up to 75 wt % based on the whole slow-release component and is coated with an enteric coating film soluble in the pH range of 5.0 to 7.0.

2. The long-acting formulation of cefaclor as claimed in claim 1, wherein said enteric coating film is soluble in a range of pH 5.5 to 6.5.

3. The long-acting formulation of cefaclor as claimed in claim 1, wherein said enteric coating film is of methyl methacrylate. methacrylic acid copolymer.

4. The long-acting formulation of cefaclor as claimed in claim 1, wherein the slow-release component is in a form of granules.

5. The long-acting formulation of cefaclor as claimed in claim 1, which is in a form of capsules filled with said mixture.

* * * * *